United States Patent [19]

Sato et al.

[11] 4,328,238

[45] May 4, 1982

[54] BENZOTHIAZOCINE AND BENZOTHIAZONINE DERIVATIVES AND USE

[75] Inventors: Yasunobu Sato; Kuniyuki Tomita; Shinsaku Kobayashi, all of Hiromachi, Japan

[73] Assignee: Sankyo Company Limited, Tokyo, Japan

[21] Appl. No.: 184,096

[22] Filed: Sep. 4, 1980

Related U.S. Application Data

[63] Continuation of Ser. No. 44,377, Jun. 1, 1979, abandoned.

[30] Foreign Application Priority Data

Jun. 5, 1978 [JP] Japan ............................. 53-67368
Jun. 5, 1978 [JP] Japan ............................. 53-67369

[51] Int. Cl.³ ................ A61K 31/395; A61K 31/55; C07D 281/10; C07D 281/18
[52] U.S. Cl. .................................... 424/275; 260/330
[58] Field of Search ................ 260/330; 424/244, 275

[56] References Cited

U.S. PATENT DOCUMENTS 3,463,774 8/1969 Wenner et al. ................ 260/330 X

Primary Examiner—Richard Raymond
Attorney, Agent, or Firm—Frishauf, Holtz, Goodman & Woodward

[57] ABSTRACT

Benzothiazocine and benzothiazonine derivatives of formula (I):

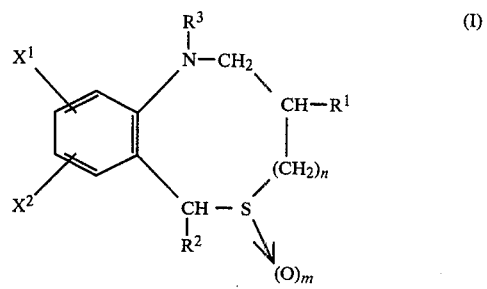

in which:
$R^1$, $R^2$ and $R^3$ are the same or different and each represents a hydrogen atom or an alkyl group;
$X^1$ and $X^2$ are the same or different and each represents a hydrogen atom, an alkyl group, an alkoxy group, an alkanesulphinyl group, an alkanesulphonyl group, a halogen atom, a trifluoromethyl group, a nitro group or a cyano group;
n is 1 or 2; and
m is 0 or 1 (excluding those compounds wherein:
$R^1$, $R^2$, $R^3$, $X^1$ and $X^2$ all represent hydrogen atoms;
n is 1 and m is 0; and wherein:
$R^1$ and $R^2$ both represent hydrogen atoms;
$R^3$ represents a hydrogen atom or a methyl group;
$X^1$ represents a chlorine atom at the 9-position;
$X^2$ represents a hydrogen atom;
n is 1; and
m is 0)

and acid addition salts thereof are novel compounds which have been found to suppress gastric secretions and are thus useful in the treatment and prevention of gastric ulcers. Compounds in which m is 0 may be prepared by reacting a corresponding ω-substituted thioalkylaniline derivative with a halogen or an active halogen compound and then condensing the product and, if necessary, introducing an alkyl group at the 1-position. Compounds in which m is 1 may be prepared by oxidizing the corresponding compound wherein m is 0.

28 Claims, No Drawings

BENZOTHIAZOCINE AND BENZOTHIAZONINE DERIVATIVES AND USE

This is a continuation of application Ser. No. 44,377 filed June 1, 1979, now abandoned.

BACKGROUND OF THE INVENTION

U.S. Pat. No. 3,463,774 discloses that certain 4,1-benzothiazepines and 5,1-benzothiazocines have useful antidepressant activity on the central nervous system. We have now surprisingly discovered that a series of new and closely related benzothiazocines and benzothiazonines reduce gastric secretions and are thus useful in the treatment and prevention of gastric ulcers. We have also discovered a new method of preparing such compounds.

BRIEF SUMMARY OF INVENTION

Compounds which may be prepared by the process of the present invention are those compounds of formula (I):

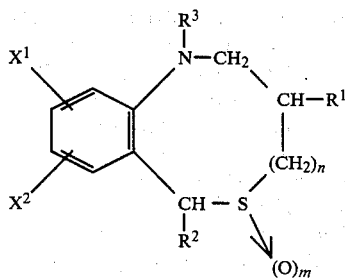

in which:

$R^1$, $R^2$ and $R^3$ are the same or different and each represents a hydrogen atom or an alkyl group;

$X^1$ and $X^2$ are the same or different and each represents a hydrogen atom, an alkyl group, an alkoxy group, an alkanesulphinyl group, an alkanesulphonyl group, a halogen atom, a trifluoromethyl group, a nitro group or a cyano group;

n is 1 or 2; and m is 0 or 1;

and pharmaceutically acceptable and addition salts thereof.

All of the compounds of formula (I) are new except those in which:

$R^1$, $R^2$, $R^3$, $X^1$ and $X^2$ all represent hydrogen atoms;
n is 1; and
m is 0;
and
$R^1$ and $R^2$ represent hydrogen atoms;
$R^3$ represents a hydrogen atom or a methyl group;
$X^1$ represents a chlorine atom at the 9-position;
$X^2$ represents a hydrogen atom;
n is 1; and
m is 0.

These new compounds also form part of the present invention.

The compounds of formula (I) may be prepared by the following steps:

(i) reacting a compound of formula (II):

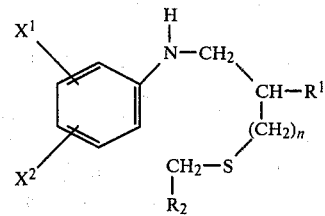

(in which $R^1$, $R^2$, $X^1$, $X^2$ and n are as defined above) with a halogen or with an active halogen compound to give a compound of formula (III):

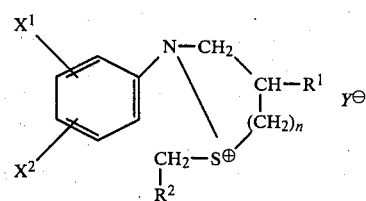

(in which Y represents a halogen atom and $R^1$, $R^2$, $X^1$, $X^2$ and n are defined above);

(ii) condensing the compound of formula (III);

(iii) if necessary, alkylating the compound obtained in step (ii) or acylating that compound and reducing the acylated compound to produce a compound of formula (Ia):

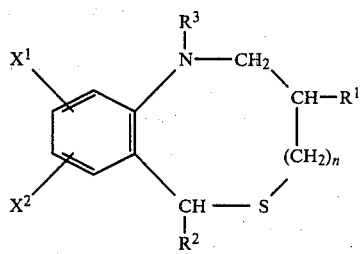

(in which $R^1$, $R^2$, $R^3$, $X^1$, $X^2$ and n are as defined above); and (iv) if desired, oxidizing said compound of formula (Ia) to produce a compound of formula (Ib):

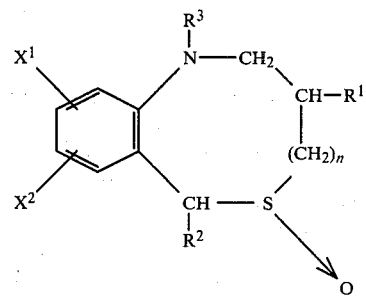

(in which $R^1$, $R^2$, $R^3$, $X^1$, $X^2$ and n are as defined above).

Pharmaceutically acceptable salts of the compound of formula (I) thus obtained may be produced by conventional methods.

DETAILED DESCRIPTION OF THE INVENTION

In the compounds of the invention, $R^1$, $R^2$ and $R^3$, which may be the same or different, preferably each represent a hydrogen atom or a straight or branched chain alkyl group having from 1 to 4 carbon atoms, for example a methyl, ethyl, n-propyl, isopropyl, n-butyl or isobutyl group. $R^2$ and $R^3$, where they represent an alkyl group, more preferably represent an alkyl group having from 1 to 3 carbon atoms.

Where $X^1$ or $X^2$ represents an alkyl group, this is preferably a lower alkyl group having from 1 to 4 carbon atoms, which may be a straight or branched chain group. Examples include the methyl, ethyl, n-propyl, isopropyl, n-butyl, isobutyl and t-butyl groups.

Where $X^1$ or $X^2$ represents an alkoxy group, this is preferably a lower alkoxy group having from 1 to 4 carbon atoms and it may be a straight or branched chain group. Examples include the methoxy, ethoxy, n-propoxy, isopropoxy and n-butoxy groups.

Where $X^1$ or $X^2$ represents an alkanesulphinyl group, this is preferably a lower alkanesulphinyl group having from 1 to 4 carbon atoms, of which the alkyl moiety may be straight or branched chain. Examples of such groups include the methanesulphinyl, ethanesulphinyl, propanesulphinyl, 1-methylethanesulphinyl, butanesulphinyl and 2-methylpropanesulphinyl groups.

Where $X^1$ or $X^2$ represents an alkanesulphonyl group, this is preferably a lower alkanesulphonyl group having from 1 to 4 carbon atoms, of which the alkyl moiety may be straight or branched chain. Examples of such groups include the methanesulphonyl, ethanesulphonyl, propanesulphonyl, 1-methylethanesulphonyl, butanesulphonyl and 2-methylpropanesulphonyl groups.

Where $X^1$ or $X^2$ represents a halogen atom, this may be a fluorine, chlorine, bromine or iodine atom.

A preferred class of compounds according to the present invention are those compounds of formula (I) in which:

$R^1$, $R^2$ and $R^3$ are the same or different and each represents a hydrogen atom or a methyl group;

$X^1$ represents a group at the 8-position and is a hydrogen atom, a $C_1$–$C_4$ alkyl group, a $C_1$–$C_4$ alkoxy group, a $C_1$–$C_4$ alkanesulphinyl group, a $C_1$–$C_4$ alkanesulphonyl group, a halogen atom, a trifluoromethyl group, a nitro group or a cyano group (more preferably a hydrogen atom, a $C_1$–$C_4$ alkyl group, a $C_1$–$C_4$ alkoxy group, a $C_1$–$C_4$ alkanesulphonyl group, a halogen atom, a trifluoromethyl group, a nitro group or a cyano group);

$X^2$ represents a hydrogen atom;

n is 1; and m is 0 or 1.

Amongst these compounds, a particularly preferred class of compounds are those in which:

$R^1$ and $R^3$, which are the same or different, each represents a hydrogen atom or a methyl group;

$R^2$ represents a methyl group;

$X^1$ represents a substituent at the 8-position and is a $C_1$–$C_4$ alkanesulphonyl group, a halogen atom, a trifluoromethyl group, a nitro group or a cyano group;

$X^2$ represents a hydrogen atom;

n is 1; and m is 0.

A further particularly preferred class of compounds are those in which:

$R^1$, $R^2$ and $R^3$ all represent hydrogen atoms;

$X^1$ represents a substituent at the 8-position and is a hydrogen atom, a $C_1$–$C_4$ alkoxy group, a halogen atom, a trifluoromethyl group, a nitro group or a cyano group;

$X^2$ represents a hydrogen atom;

n is 1; and m is 1.

The compounds of formula (I) can be converted to their pharmaceutically acceptable acid addition salts by methods well-known in the art for the salification of this type of compound. Examples of such salts are salts with inorganic acids, for example the hydrochlorides, sulphates or phosphates, and salts with organic acids, for example the maleates and tartrates.

Examples of compounds according to the present invention are those listed below:

1. 1,3,4,6-Tetrahydro-6-methyl-2H-5,1-benzothiazocine and its hydrochloride.
2. 1,3,4,6-Tetrahydro-8-methyl-2H-5,1-benzothiazocine and its hydrochloride.
3. 1,3,4,6-Tetrahydro-6,8-dimethyl-2H-5,1-benzothiazocine and its hydrochloride.
4. 8-Ethyl-1,3,4,6-tetrahydro-6-methyl-2H-5,1-benzothiazocine and its hydrochloride.
5. 1,3,4,6-Tetrahydro-6-methyl-8-n-propyl-2H-5,1-benzothiazocine and its hydrochloride.
6. 8-n-Butyl-1,3,4,6-tetrahydro-6-methyl-2H-5,1-benzothiazocine and its hydrochloride.
7. 1,3,4,6-Tetrahydro-6,8,9-trimethyl-2H-5,1-benzothiazocine and its hydrochloride.
8. 1,3,4,6-Tetrahydro-8-methoxy-2H-5,1-benzothiazocine and its hydrochloride.
9. 1,3,4,6-Tetrahydro-8-methanesulphonyl-6-methyl-2H-5,1-benzothiazocine and its hydrochloride.
10. 8-Fluoro-1,3,4,6-tetrahydro-6-methyl-2H-5,1-benzothiazocine and its hydrochloride.
11. 8-Chloro-1,3,4,6-tetrahydro-2H-5,1-benzothiazocine and its hydrochloride.
12. 7-Chloro-1,3,4,6-tetrahydro-6-methyl-2H-5,1-benzothiazocine and its hydrochloride.
13. 8-Chloro-1,3,4,6-tetrahydro-6-methyl-2H-5,1-benzothiazocine and its hydrochloride.
14. 9-Chloro-1,3,4,6-tetrahydro-6-methyl-2H-5,1-benzothiazocine and its hydrochloride.
15. 8-Chloro-1,3,4,6-tetrahydro-3,6-dimethyl-2H-5,1-benzothiazocine and its hydrochloride.
16. 8-Chloro-1,3,4,6-tetrahydro-6,10-dimethyl-2H-5,1-benzothiazocine and its hydrochloride.
17. 8-Chloro-1,3,4,6-tetahydro-1,6-dimethyl-2H-5,1-benzothiazocine and its hydrochloride.
18. 8-Bromo-1,3,4,6-tetrahydro-6-methyl-2H-5,1-benzothiazocine and its hydrochloride.
19. 10-Bromo-1,3,4,6-tetrahydro-6,8-dimethyl-2H-5,1-benzothiazocine and its hydrochloride.
20. 1,3,4,6-Tetrahydro-8-iodo-6-methyl-2H-5,1-benzothiazocine and its hydrochloride.
21. 8,10-Difluoro-1,3,4,6-tetrahydro-6-methyl-2H-5,1-benzothiazocine and its hydrochloride.
22. 7,8-Dichloro-1,3,4,6-tetrahydro-6-methyl-2H-5,1-benzothiazocine and its hydrochloride.
23. 8,10-Dichloro-1,3,4,6-tetrahydro-6-methyl-2H-5,1-benzothiazocine and its hydrochloride.
24. 8-Bromo-10-chloro-1,3,4,6-tetrahydro-6-methyl-2H-5,1-benzothiazocine and its hydrochloride.
25. 1,3,4,6-Tetrahydro-6-methyl-8-trifluoromethyl-2H-5,1-benzothiazocine and its hydrochloride.

26. 8-Chloro-1,3,4,6-tetrahydro-6-methyl-7-trifluoromethyl-2H-5,1-benzothiazocine and its hydrochloride.
27. 8-Chloro-1,3,4,6-tetrahydro-6-methyl-9-trifluoromethyl-2H-5,1-benzothiazocine and its hydrochloride.
28. 8-Chloro-1,3,4,6-tetrahydro-6-methyl-10-trifluoromethyl-2H-5,1-benzothiazocine and its hydrochloride.
29. 10-Chloro-1,3,4,6-tetrahydro-6-methyl-7-trifluoromethyl-2H-5,1-benzothiazocine and its hydrochloride.
30. 1,3,4,6-Tetrahydro-6-methyl-8-nitro-2H-5,1-benzothiazocine and its hydrochloride.
31. 1,3,4,6-Tetrahydro-6,8-dimethyl-9-nitro-2H-5,1-benzothiazocine and its hydrochloride.
32. 8-Fluoro-1,3,4,6-tetrahydro-6-methyl-10-nitro-2H-5,1-benzothiazocine and its hydrochloride.
33. 8-Fluoro-1,3,4,6-tetrahydro-6-methyl-9-nitro-2H-5,1-benzothiazocine and its hydrochloride.
34. 8-Chloro-1,3,4,6-tetrahydro-6-methyl-9-nitro-2H-5,1-benzothiazocine and its hydrochloride.
35. 8-Chloro-1,3,4,6-tetrahydro-6-methyl-10-nitro-2H-5,1-benzothiazocine and its hydrochloride.
36. 10-Chloro-1,3,4,6-tetrahydro-6-methyl-7-nitro-2H-5,1-benzothiazocine and its hydrochloride.
37. 10-Chloro-1,3,4,6-tetrahydro-6-methyl-8-nitro-2H-5,1-benzothiazocine and its hydrochloride.
38. 10-Bromo-1,3,4,6-tetrahydro-6-methyl-8-nitro-2H-5,1-benzothiazocine and its hydrochloride.
39. 1,3,4,6-Tetrahydro-6-methyl-10-nitro-8-trifluoromethyl-2H-5,1-benzothiazocine and its hydrochloride.
40. 8-Cyano-1,3,4,6-tetrahydro-6-methyl-2H-5,1-benzothiazocine and its hydrochloride.
41. 1,2,3,4,5,7-Hexahydro-6,1-benzothiazonine and its hydrochloride.
42. 8-Fluoro-1,3,4,6-tetrahydro-2H-5,1-benzothiazocine and its hydrochloride.
43. 7-Chloro-1,3,4,6-tetrahydro-2H-5,1-benzothiazocine and its hydrochloride.
44. 10-Chloro-1,3,4,6-tetrahydro-6-methyl-2H-5,1-benzothiazocine and its hydrochloride.
45. 8,9-Dichloro-1,3,4,6-tetrahydro-6-methyl-2H-5,1-benzothiazocine and its hydrochloride.
46. 6-Ethyl-1,3,4,6-tetrahydro-2H-5,1-benzothiazocine and its hydrochloride.
47. 1,2,3,4,5,7-Hexahydro-7-methyl-6,1-benzothiazonine and its hydrochloride.
48. 8-Chloro-1-ethyl-1,3,4,6-tetrahydro-6-methyl-2H-5,1-benzothiazocine and its hydrochloride.
49. 1,3,4,6-Tetrahydro-8-nitro-2H-5,1-benzothiazocine and its hydrochloride.
50. 8-Cyano-1,3,4,6-tetrahydro-2H-5,1-benzothiazocine and its hydrochloride.
51. 1,3,4,6-Tetrahydro-2H-5,1-benzothiazocine-S-oxide.
52. 1,3,4,6-Tetrahydro-8-methyl-2H-5,1-benzothiazocine-S-oxide.
53. 8-Fluoro-1,3,4,6-tetrahydro-2H-5,1-benzothiazocine-S-oxide.
54. 8-Chloro-1,3,4,6-tetrahydro-2H-5,1-benzothiazocine-S-oxide.
55. 8-Bromo-1,3,4,6-tetrahydro-6-methyl-2H-5,1-benzothiazocine-S-oxide.
56. 7,8-Dichloro-1,3,4,6-tetrahydro-2H-5,1-benzothiazocine-S-oxide.
57. 8-Bromo-10-chloro-1,3,4,6-tetrahydro-2H-5,1-benzothiazocine-S-oxide.
58. 1,3,4,6-Tetrahydro-8-trifluoromethyl-2H-5,1-benzothiazocine-S-oxide.
59. 1,3,4,6-Tetrahydro-10-nitro-8-trifluoromethyl-2H-5,1-benzothiazocine-S-oxide.
60. 1,3,4,6-Tetrahydro-8-nitro-2H-5,1-benzothiazocine-S-oxide.
61. 8-Cyano-1,3,4,6-tetrahydro-2H-5,1-benzothiazocine-S-oxide.
62. 1,3,4,6-Tetrahydro-8-methoxy-2H-5,1-benzothiazocine-S-oxide.
63. 8-Chloro-1,3,4,6-tetrahydro-1-methyl-2H-5,1-benzothiazocine-S-oxide.
64. 1,2,3,4,5,7-Hexahydro-6,1-benzothiazonine-S-oxide.
65. 8-Chloro-1,3,4,6-tetrahydro-1-methyl-2H-5,1-benzothiazocine and its hydrochloride.

The compounds of the invention are hereinafter referred to by the numbers assigned to them in the above list. The free bases are referred to simply by the number assigned above; their hydrochlorides are referred to by the assigned number together with the suffix "HCl". Of these compounds, the following are preferred: 9, 10, 13, 15, 17, 18, 20, 25, 30, 40 and their hydrochlorides, 51, 53, 54, 55, 58, 60, 61 and 62.

As already noted, the compounds of the invention have the ability to suppress gastric secretion. This was tested using Shay rats by the Shay method [H. Shay : Gastroenterology, Volume 5, page 43 (1945)], the compounds tested being administered at a dose of 40 mg/kg intraduodenally. The results obtained are shown in Table 1, in which the compounds of the invention are identified as described above and comparable results are also given, for purposes of comparison, for a test using the known anti-ulcer agent, Cimetidine.

TABLE 1

| Compound | Suppression Rate (%) |
|---|---|
| 1 | 84 |
| 2HCl | 85 |
| 3HCl | 91 |
| 4HCl | 92 |
| 5HCl | 73 |
| 6HCl | 72 |
| 7 | 66 |
| 8HCl | 34 |
| 10HCl | 80 |
| 11 | 49 |
| 12HCl | 68 |
| 13HCl | 86 |
| 14HCl | 80 |
| 15HCl | 77 |
| 17HCl | 78 |
| 18HCl | 75 |
| 22HCl | 79 |
| 25 | 91 |
| 30 | 37 |
| 40 | 46 |
| 41 | 75 |
| 51 | 80 |
| 52 | 87 |
| 53 | 74 |
| 54 | 74 |
| 55 | 36 |
| 60 | 43 |
| 61 | 47 |
| 62 | 69 |
| 64 | 93 |
| Cimetidine | 29 |

It is apparent from the test data reported in the above Table that the compounds of the invention are excellent suppressors of gastric secretions, their activity uniformly being substantially above, in some cases by several times, the activity of the known anti-ulcer agent, Cimetidine. The compounds of the invention are therefore of value as anti-ulcer agents, for the treatment and/or prevention of gastric ulcers. The compounds can be administered orally as tablets, capsules, granules, powders or syrups or parenterally as injections. The dosage will, of course, vary depending upon the disease and the age and body weight of the patient. However, for oral administration, the dose would normally be from 100 mg to 1,000 mg per day in a single dose or divided doses. For parenteral administration, the dose would normally be from 10 mg to 100 mg per day and this can be administered by subcutaneous, intramuscular or intravenous injection.

Thus, the invention further provides a pharmaceutical composition comprising a novel compound of formula (I) or a pharmaceutically acceptable salt thereof in admixture with a pharmaceutically acceptable carrier or diluent.

Compounds of formula (I) in which m is 0, that is to say compounds of formula (Ia) as defined above, can be prepared by reacting a compound of formula (II), as defined above, with a halogen or with an active halogen compound to form a compound of formula (III), as previously defined, and then condensing this compound of formula (III). This produces a compound of formula (Ia) in which $R^3$ represents a hydrogen atom; this hydrogen atom may be converted to an alkyl group by a simple alkylation reaction or by acylation followed by reduction of the introduced acyl group.

The compounds of formula (III) are new compounds and also form part of the present invention.

The first step in this reaction sequence may be carried out by contacting the ω-substituted thioalkylaniline derivative of general formula (II) with the halogen or active halogen compound, preferably in the presence of a solvent. Examples of suitable active halogen compounds include: N-haloaliphatic acid imides, such as N-chlorosuccinimide or N-bromosuccinimide; alkaline earth metal hypochlorites, such as calcium hypochlorite; alkali metal hypochlorites, such as sodium hypochlorite; t-butyl hypochlorite; or N-halosulphonamides, such as chloramine T or dichloramine T. There is no particular limitation on the nature of the solvent employed for this reaction, provided that it does not adversely affect the reaction; we prefer to use a halogenated aliphatic hydrocarbon, such as methylene chloride, chloroform or carbon tetrachloride. The reaction will proceed completely below room temperature, but is may be carried out at any temperature up to boiling point of the solvent employed. The time required for the reaction will depend upon the reaction temperature, and may vary from 5 minutes to 1 hour.

The new compound of formula (III) produced by this reaction may be recovered from the reaction mixture by conventional means. For example, after completion of the reaction, it may be recovered by evaporating off the solvent under reduced pressure. Alternatively, the reaction mixture per se can be used in the next step.

The next step of the reaction consists of condensing the compound of formula (III), which may be effected by contacting the compound of formula (III) with a base in the presence of an inert solvent. Suitable bases include: alkali metal hydroxides, such as sodium hydroxide or potassium hydroxide; alkali metal alkoxides, such as sodium methoxide or sodium ethoxide, trialkylamines, such as triethylamine; and other organic bases, such as 1,5-diazabicyclo[5.4.0]undecene-5. Suitable inert solvents include: halogenated aliphatic hydrocarbons, such as methylene chloride, chloroform or carbon tetrachloride; water; and alcohols, such as methanol or ethanol; it is, of course, also possible to employ a mixture of any two or more of these solvents. The reaction will proceed completely below room temperature and we prefer to carry it out at a temperature from 0° to 10° C. The time required for the reaction will vary depending upon the reaction temperature, but is usually from 2 minutes to 1 hour.

The third step in this reaction sequence is designed, if desired, to convert the resulting compound of formula (Ia) in which $R^3$ represents a hydrogen atom to a corresponding compound in which $R^3$ represents an alkyl group. This conversion may be carried out by conventional means by contacting the product of the previous step with an alkylating agent or by contacting it with an acylating agent and then reducing the introduced acyl group. There is no particular limitation upon the nature of the alkylating agent employed and any conventional alkylating agent capable of introducing the desired alkyl group may be used. Examples include: the preferred methylating agent, a mixture of formic acid and formalin; alkyl halides, such as methyl iodide, ethyl iodide or isopropyl bromide; and alkylsulphuric acids, such as diemthylsulphuric acid or diethylsulphuric acid. Where the alkylating agent is an alkyl halide or an alkylsulphuric acid, the reaction is preferably carried out in the presence of a base, for example: an alkali metal hydroxide, such as sodium hydroxide or potassium hydroxide; an alkali metal carbonate, such as sodium carbonate or potassium carbonate, an alkali metal hydride, such as sodium hydride or potassium hydride; or an alkali metal alkoxide, such as sodium methoxide or sodium ethoxide.

The alternative means of introducing an alkyl group is by acylation followed by reduction. There is no particular limitation upon the nature of the acylating agent employed and any conventional acylating agent capable of introducing the desired acyl group may be used. Preferred acylating agents are: acyl halides, such as acetyl chloride or propionyl chloride; and acid anhydrides, such as acetic anhydride or propionic anhydride. This reaction is preferably carried out in the presence of a base, for example: an alkali metal hydroxide, such as sodium hydroxide or potassium hydroxide; an alkali metal carbonate, such as sodium carbonate or potassium carbonate; an alkali metal hydride, such as sodium hydride or potassium hydride; or an alkali metal alkoxide, such as sodium methoxide or sodium ethoxide. The subsequent reduction of the acyl group thus introduced may be carried out with any reducing agent capable of reducing an acyl group to an alkyl group and there is no particular limitation upon the nature of the reducing agent, provided that it does not affect other parts of the molecule. Suitable reducing agents are alkali metal aluminium hydrides (such as lithium aluminium hydride or sodium aluminium hydride) or diborane.

The compounds of formula (Ia) obtained in either the second or third of the steps of the above reaction sequence may be recovered from their reaction mixture by conventional means. A suitable recovery procedure comprises, for example: concentrating the reaction mixture by evaporation under reduced pressure; extracting the residue with an organic solvent, such as chloroform; washing the extract with water; and distilling off the solvent under reduced pressure to give crystals of the desired compound. Where the product is an oil, it is preferably converted to a salt, which can be recovered from the mixutre by conventional techniques. The compounds thus obtained may, if desired, be further purified by, for example, recrystallization or column chromatography.

Compounds of formula (I) in which m is 1, that is to say compounds of formula (Ib), can be prepared by oxidizing the corresponding compound of formula (Ia). The oxidation is preferably carried out in the presence of a solvent, the nature of which is not critical, provided that it does not adversely affect the reaction. Suitable solvents are alcohols, such as methanol or ethanol. Suitable oxidizing agents include; sodium periodate, t-butyl hypochlorite; organic peracids, such as perbenzoic acid or m-chloroperbenzoic acid; hydrogen peroxide; N-haloaliphatic acid imides, such as N-chlorosuccinimide; or iodosobenzene. The reaction may be carried out over a wide temperature range, but proceeds completely at room temperature, which is a convenient reaction temperature to employ. The time required for the reaction will depend upon the reaction temperature, but will normally be from 30 minutes to 5 hours.

After completion of the reaction, the desired product may be recovered by conventional means and, if necessary, further purified by recrystallization or column chromatography.

The compounds of formula (I) form acid addition salts; these may be prepared by methods well-known in the art for preparing pharmaceutically acceptable acid addition salts of basic compounds. Examples of suitable salts are inorganic salts (such as the hydrochlorides, sulphates and phosphates) and organic salts (such as the maleates and tartrates).

The compounds of formula (II), which are used as starting materials in the process of the invention are novel compounds and also form part of the present invention. They can be prepared, for example, by any of the reactions shown in the scheme below:

The reaction in step (a) in which aniline or an aniline derivative of formula (IV) is reacted with an ω-haloaliphatic acid chloride to produce an ω-haloaliphatic acid anilide of formula (V) can be carried out by the method reported in Ber. 60, 880 (1927) by F. Mayer, L. von Ziitpher and H. Philipps.

The reaction in step (b) is carried out by contacting the aniline or aniline derivative (IV) with an ω-substituted thioaliphatic acid chloride. The reaction is normally carried out in the presence of a solvent, but the nature of the solvent is not critical, provided that it does not adversely affect the reaction. Preferred solvents are aliphatic ketones, such as acetone or methyl ethyl ketone. The reaction temperature is also not critical, but we prefer to employ a temperature within the range from 20° C. to 100° C. The time required for the reaction, which will depend upon the reaction temperature and other reaction conditions, will generally be within the range from 30 minutes to 5 hours.

The reaction in step (c) is carried out by contacting the ω-haloaliphatic acid anilide (V), prepared in step (a), with a mercaptan in the presence of an acid binding agent, which is an organic or organic base. The reaction is suitably carried out in the presence of a solvent, the nature of which is not critical, provided that it does not adversely affect the reaction; in general, we prefer to use an ether, such as dioxan or tetrahydrofuran. The reaction temperature is also not critical and the reaction is therefore normally carried out at room temperature or at the boiling point of the solvent employed. The time required for the reaction will vary depending upon the reaction temperature, but will normally be from 1 hour to 3 days.

The reaction in step (d) is carried out by vontacting the ω-substituted thioaliphatic acid anilide derivative of formula (VI), prepared by step (b) or (c), with a reducing agent. Preferred reducing agents are alkali metal

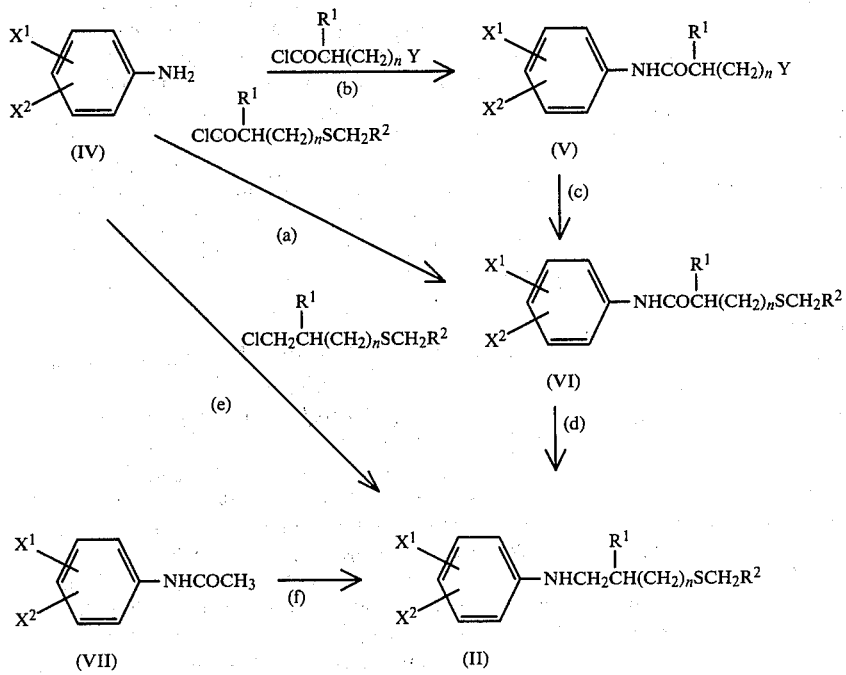

In the above formulae, Y represents a halogen atom and $R^1$, $R^2$, $X^1$, $X^2$ and n are as defined above. The compounds of formula (VI) are also new compounds.

aluminium hydrides, such as lithium aluminium hydride or sodium aluminium hydride. The reaction is normally carried out in the presence of a solvent, whose nature is not critical, provided that it does not adversely affect the reaction; ethers, such as diethyl ether or tetrahydrofuran are preferred. The reaction temperature is not critical, but we normally prefer to carry out the reaction at a temperature from 20° C. to 100° C. The time required for the reaction, which will vary depending upon reaction temperature and other conditions, is normally from 30 minutes to 5 hours.

The reaction in step (e) is carried out by contacting aniline or an aniline derivative of formula (IV) with an ω-substituted thioalkyl halide. The reaction is normally carried out in the presence of a solvent, whose nature is not critical, provided that it does not adversely affect the reaction; N,N-dialkylaliphatic acid amides, such as dimethylformamide or dimethylacetamide are preferred. The reaction temperature is conveniently from 100° C. to 200° C. and the time required for the reaction is generally from 1 hour to 10 hours.

The reaction in step (f) is carried out by contacting an acid anilide derivative of general formula (VII) with an ω-substituted thioalkyl halide in the presence of an acid binding agent (for example: an alkali metal hydride, such as sodium hydride; or an alkali metal amide, such as sodium amide) and then deacetylating the resulting product. The reaction is normally carried out in the presence of a solvent, but the nature of this is not critical, provided that it does not adversely affect the reaction; N,N-dialkylaliphatic acid amides, such as dimethylformamide or dimethylacetamide, are preferred. The reaction temperature is not critical and we normally prefer to employ a temperature from 100° to 200° C. The deacetylation proceeds simultaneously with the former reaction, but alternatively, it is possible to carry out the deacetylation by contacting the product of the former reaction with a mineral acid, such as hydrochloric acid or sulphuric acid.

The desired compound obtained by any of the methods described above may then be recovered by conventional means and, if necessary, further purified by, for example, recrystallization, distillation under reduced pressure and column chromatography.

The invention is further illustrated by the following Examples, which illustrate the preparation of the compounds of the invention, and the following Preparations, which illustrate the preparation of certain starting materials.

EXAMPLE 1

1,3,4,6-Tetrahydro-8-methyl-2H-5,1-benzothiazocine hydrochloride (Compound 2HCl)

9.8 g of N-(3-methylthio)propyl-p-toluidine were added dropwise to a solution of 6.7 g of N-chlorosuccinimide in 300 ml of methylene chloride, keeping the mixture below 10° C. The mixture was then stirred for 5 minutes, after which 12 ml of a 28% w/v methanolic solution of sodium methoxide was added dropwise, again keeping the mixture below 10° C. After stirring the mixture for 5 minutes, it was washed with water and dried; the solvent was then evaporated off. The residue was purified by silica gel chromatography and converted to the crystalline hydrochloride. This salt was recrystallized from a 1:1 by volume mixture of methanol and acetone to give 10 g of crystals melting at 197°–202° C. (with decomposition).

Elemental Analysis: Calculated for $C_{11}H_{15}NS \cdot HCl$: C, 57.50%; H, 7.01%; N, 6.09%; Cl, 15.42%; S, 13.95%. Found: C, 57.35%; H, 7.06%; N, 5.89%; Cl, 15.71%; S, 13.70%.

EXAMPLE 2

8-Fluoro-1,3,4,6-tetrahydro-2H-5,1-benzothiazocine hydrochloride (Compound 42HCl)

1.3 g of N-(3-methylthio)propyl-p-fluoroaniline were added dropwise to a solution of 1.2 g of N-bromosuccinimide in 100 ml of methylene chloride, whilst keeping the mixture below 8° C. The mixture was then stirred for 5 minutes, after which 2 ml of a 28% w/v methanolic solution of sodium methoxide were added dropwise, whilst maintaining the mixture below 5° C. The mixture was stirred for 10 minutes, after which it was treated in the same manner as described in Example 1 to give an oil. This oil was converted to the crystalline hydrochloride, which was recrystallized from a 3:2 by volume mixture of methylene chloride and acetone to give 1.4 g of crystals of the desired Compound 42HCl, melting at 148°–150° C.

Elemental Analysis: Calculated for $C_{10}H_{12}FNS \cdot HCl$: C, 51.38%; H, 5.60%; N, 5.99%; Cl, 15.16%; F, 8.12%; S, 13.71%. Found: C, 51.37%; H, 5.54%; N, 6.06%; Cl, 15.23%; F, 7.96%; S, 13.64%.

EXAMPLE 3

7-Chloro-1,3,4,6-tetrahydro-2H-5,1-benzothiazocine (Compound 43)

14.0 g of N-(3-methylthio)propyl-m-chloroaniline were added dropwise to a solution of 8.7 g of N-chlorosuccinimide in 300 ml of methylene chloride, whist maintaining the mixture at a temperature below 10° C. The mixture was then stirred for 5 minutes, after which 10 ml of a 28% w/v methanolic solution of sodium methoxide were added dropwise, whilst maintaining the temperature of the mixture below 10° C. After stirring the reaction mixture for 5 minutes, it was concentrated by evaporating off the solvent under reduced pressure and then the residue was isolated and purified by silica gel column chromatography. The crystals thus obtained were recrystallized from a 3:2 by volume mixture of methylene chloride and n-hexane to give 5 g of crystals of Compound 43, melting at 71°–73° C.

Elemental Analysis: Calculated for $C_{10}H_{12}ClNS$: C, 56.20%; H, 5.66%; N, 6.55%; S, 15.00%; Cl, 16.59%. Found: C, 56.03%; H, 5.65%; N, 6.67%; S, 15.14%; Cl, 16.82%.

EXAMPLE 4

8-Chloro-1,3,4,6-tetrahydro-2H-5,1-benzothiazocine (Compound 11)

21.5 g of p-chloro-N-(3-methylthio)propylaniline were added to a solution of 13.3 g of N-chlorosuccinimide in 800 ml of methylene chloride, whilst maintaining the mixture below 5° C. The mixture was stirred for 5 minutes, after which 25 ml of a 28% w/v methanolic solution of sodium methoxide were added, maintaining the mixture below 5° C. After stirring the mixture for 5 minutes, it was treated as described in Example 3, to give crude crystals. These were recrystallized from a 3:2 by volume mixture of diethyl ether and n-hexane to give 18.6 g of crystals of the desired Compound 11, melting at 54°–55° C.

Elemental Analysis: Calculated for $C_{10}H_{12}ClNS$: C, 56.20%; H, 5.66%; N, 6.55%; S, 15.00%; Cl, 16.59%.

Found: C, 56.34%; H, 5.64%; N, 6.59%; S, 14.91%; Cl, 16.69%.

EXAMPLE 5

1,3,4,6-Tetrahydro-6-methyl-2H-5,1-benzothiazocine (Compound 1)

1.95 g of N-(3-ethylthio)propylaniline were added to a solution of 1.33 g of N-chlorosuccinimide in 150 ml of methylene chloride, whilst maintaining the temperature of the mixture at 3°–5° C. After stirring the mixture for 5 minutes, 2 ml of a 28% w/v methanolic solution of sodium methoxide were added dropwise, whilst maintaining the mixture below 5° C. The reaction mixture was then treated as described in Example 3, to give 1.25 g of crystals of the desired Compound 1, melting at 72°–74° C.

Elemental Analysis: Calculated for $C_{11}H_{15}NS$: C, 68.35%; H, 7.82%; N, 7.25%; S, 16.59%. Found: C, 68.47%; H, 7.89%; N, 7.32%; S, 16.57%.

EXAMPLE 6

1,3,4,6-Tetrahydro-6,8-dimethyl-2H-5,1-benzothiazocine hydrochloride (Compound 3HCl)

2.9 g of N-(3-ethylthio)propyl-p-toluidine were added to a solution of 1.6 g of N-chlorosuccinimide in 100 ml of methylene chloride, whilst maintaining the mixture below 10° C. The mixture was then stirred for 10 minutes, after which 2.5 ml of triethylamine were added, maintaining the mixture below 5° C. After stirring the mixture for 10 minutes, it was washed with water and dried and the solvent was evaporated off. The residue was purified by silica gel column chromatography (eluted with a 5:1 by volume mixture of benzene and ethyl acetate) to give an oil. This oil was converted to the crystalline hydrochloride and this salt was recrystallized from a 1:1 by volume mixture of methanol and acetone to give 1.4 g of the desired Compound 3HCl in the form of crystals melting at 220°–222° C. (with decomposition).

Elemental analysis: Calculated for $C_{12}H_{17}NS.HCl$: C, 59.11%; H, 7.44%; N, 5.74%; S, 13.15%; Cl, 14.54%. Found: C, 59.08%; H, 7.48%; N, 5.54%; S, 13.12%; Cl, 14.45%.

EXAMPLE 7

8-Ethyl-1,3,4,6-tetrahydro-6-methyl-2H-5,1-benzothiazocine hydrochloride (Compound 4HCl)

2.4 g of p-ethyl-N-(3-ethylthio)propylaniline were added to a solution of 1.45 g of N-chlorosuccinimide in 100 ml of methylene chloride, whilst maintaining the temperature of the mixture below 5° C. The mixture was then stirred for 5 minutes, after which 1.5 ml of triethylamine were added dropwise, maintaining the mixture below 5° C. After stirring the mixture for 5 minutes, it was washed with water and dried. The solvent was then evaporated off and 10% w/v methanolic hydrogen chloride was added to the residue to produce a precipitate, which was recrystallized from methanol to give 1.8 g of the desired Compound 4HCl in the form of crystals melting at 218°–220° C. (with decomposition).

Elemental analysis: Calculated for $C_{13}H_{19}NS.HCl$: C, 60.56%; H, 7.81%; N, 5.43%; S, 12.43%; Cl, 13.75%. Found: C, 60.58%; H, 7.84%; N, 5.64%; S, 12.63%; Cl, 13.76%.

EXAMPLE 8

1,3,4,6-Tetrahydro-6-methyl-8-n-propyl-2H-5,1-benzothiazocine hydrochloride (Compound 5HCl)

4.5 g of N-(3-ethylthio)propyl-p-propylaniline were added to a solution of 2.5 g of N-chlorosuccinimide in 150 ml of methylene chloride, whilst maintaining the temperature of the mixture below 5° C. After stirring the mixture for 5 minutes, 4 ml of triethylamine were added, again maintaining the temperature below 5° C. The reaction mixture was then treated as described in Example 7, to give 2.7 g of the desired Compound 5HCl in the form of crystals melting at 200°–203° C. (with decomposition).

Elemental analysis: Calculated for $C_{14}H_{21}NS.HCl$: C, 61.85%; H, 8.16%; N, 5.15%; S, 11.79%; Cl, 13.04%. Found: C, 61.61%; H, 8.16%; N, 5.15%; S, 11.95%; Cl, 13.16%.

EXAMPLE 9

8-n-Butyl-1,3,4,6-tetrahydro-6-methyl-2H-5,1-benzothiazocine hydrochloride (Compound 6HCl)

7.5 g of p-butyl-N-(3-ethylthio)propylaniline were added to a solution of 4 g of N-chlorosuccinimide in 200 ml of methylene chloride, whilst maintaining the temperature of the mixture below 7° C. 5 ml of triethylamine were added to the solution, maintaining the temperature below 5° C. After this, the reaction mixture was treated as described in Example 7 and the crude product was recrystallized from a 1:1 by volume mixture of methanol and acetone to give 4.6 g of the desired Compound 6HCl in the form of crystals melting at 180°–182° C. (with decomposition).

Elemental analysis: Calculated for $C_{15}H_{23}NS.HCl$: C, 63.02%; H, 8.46%; N, 4.90%; S, 11.22%; Cl, 12.40%. Found: C, 62.75%; H, 8.41%; N, 4.96%; S, 11.48%; Cl, 12.32%.

EXAMPLE 10

1,3,4,6-Tetrahydro-6,8,9-trimethyl-2H-5,1-benzothiazocine (Compound 7)

6.1 g of N-(3-ethylthio)propyl-3,4-xylidine were added to a solution of 3.6 g of N-chlorosuccinimide in 200 ml of methylene chloride, whilst maintaining the temperature below 10° C. The mixture was stirred for 5 minutes, after which 5 ml of triethylamine were added dropwise, maintaining the temperature below 8° C. The reaction mixture was then treated as described in Example 3 and the crude crystals so obtained were recrystallized from a 3:2 by volume mixture of diethyl ether and petroleum ether to give 2 g of Compound 7 in the form of crystals melting at 86°–88° C.

Elemental analysis: Calculated for $C_{13}H_{19}NS$: C, 70.53%; H, 8.65%; N, 6.32%; S, 14.48%. Found: C, 70.79%; H, 8.80%; N, 6.37%; S, 14.50%.

EXAMPLE 11

8-Fluoro-1,3,4,6-tetrahydro-6-methyl-2H-5,1-benzothiazocine hydrochloride (Compound 10HCl)

6.3 g of N-(3-ethylthio)propyl-p-fluoroaniline were added to a solution of 3.9 g of N-chlorosuccinimide in 200 ml of methylene chloride, maintaining the temperature of the mixture below 5° C. When the addition was complete, the mixture was stirred for 5 minutes and then 5 ml of triethylamine were added dropwise, maintaining the temperature below 0° C. The reaction mixture was then treated as described in Example 7 to give 4 g of the desired Compound 10HCl in the form of crystals melting at 210° C. (with decomposition).

Elemental analysis: Calculated for $C_{11}H_{14}FNS·HCl$: C, 53.32%; H, 6.10%; N, 5.65%; S, 12.94%; F, 7.66%; Cl, 14.30%. Found: C, 52.75%, H, 6.30%; N, 5.53%; S, 13.28%; F, 7.12%; Cl, 13.92%.

EXAMPLE 12

8-Chloro-1,3,4,6-tetrahydro-6-methyl-2H-5,1-benzothiazocine hydrochloride (Compound 13HCl)

3.45 g of p-chloro-N-(3-ethylthio)propylaniline were added to a solution of 2.0 g of N-chlorosuccinimide in 150 ml of methylene chloride, whilst maintaining the temperature below 10° C. The mixture was then stirred for 5 minutes, after which 4 ml of a 28% w/v methanolic solution of sodium methoxide were added dropwise, maintaining the temperature below 8° C. The reaction mixture was then treated as described in Example 7, to give 2 g of the desired Compound 13HCl in the form of crystals melting at 212°–215° C. (with decomposition).

Elemental analysis: Calculated for $C_{11}H_{14}ClNS·HCl$: C, 50.00%; H, 5.72%; N, 5.30%; S, 12.13%; Cl, 26.83%. Found: C, 50.27%; H, 5.61%; N, 5.25%; S, 12.34%; Cl, 26.92%.

EXAMPLE 13

7-Chloro-1,3,4,6-tetrahydro-6-methyl-2H-5,1-benzothiazocine hydrochloride(Compound 12HCl) and 9-Chloro-1,3,4,6-tetrahydro-6-methyl-2H-5,1-benzothiazocine hydrochloride (Compound 14HCl)

8.7 g of m-chloro-N-(3-ethylthio)propylaniline were added to a solution of 5 g of N-chlorosuccinimide in 500 ml of methylene chloride, whilst maintaining the temperature below 10° C. The mixture was then stirred for 5 minutes, after which 10 ml of a 28% w/v methanolic solution of sodium methoxide were added dropwise, maintaining the temperature below 5° C. After stirring the mixture for 10 minutes, it was treated as described in Example 1. Oils obtained from the first fraction on column chromatography were converted to the hydrochloride by conventional means and this salt was then recrystallized from methanol to give 0.8 g of the 9-chloro compound (Compound 14HCl), melting at 211°–213° C. (with decomposition).

Elemental analysis: Calculated for $C_{11}H_{14}ClNS·HCl$: C, 50.00%; H, 5.72%; N, 5.30%; S, 12.13%; Cl, 26.83%. Found: C, 49.95%; H, 5.52%; N, 5.42%; S, 12.38%; Cl, 26.84%.

Oils obtained from the second fraction were converted to the hydrochloride and this was then recrystallized from methanol to give 0.3 g of the 7-chloro compound (Compound 12HCl), melting at 218°–220° C. (with decomposition).

Elemental analysis: Calculated for $C_{11}H_{14}ClNS·HCl$: C, 50.00%; H, 5.72%; N, 5.30%; S, 12.13%; Cl, 26.83%. Found: C, 49.79%; H, 5.48%; N, 5.46%; S, 12.32%; Cl, 26.81%.

EXAMPLE 14

10-Chloro-1,3,4,6-tetrahydro-6-methyl-2H-5,1-benzothiazocine hydrochloride (Compound 44HCl)

5.4 g of o-chloro-N-(3-ethylthio)propylaniline were added to a solution of 3.35 g of N-chlorosuccinimide in 200 ml of chloroform, whilst maintaining the temperature of the solution below 10° C. After stirring the mixture for 10 minutes, 3.5 ml of triethylamine were added dropwise, again maintaining the temperature below 10° C. The reaction mixture was then treated as described in Example 7, to give 2.5 g of the desired Compound 44HCl in the form of crystals melting at 208°–210° C. (with decomposition).

Elemental analysis: Calculated for: $C_{11}H_{14}ClNS·HCl$: C, 50.00%; H, 5.72%; N, 5.30%; S, 12.13%; Cl, 26.83%. Found: C, 49.82%; H, 5.35%; N, 5.47%; S, 12.43%; Cl, 27.01%.

EXAMPLE 15

8-Chloro-1,3,4,6-tetrahydro-3,6-dimethyl-2H-5,1-benzothiazocine hydrochloride (Compound 15HCl)

10.5 g of p-chloro-N-(3-ethylthio-2-methyl)-propylaniline were added to a solution of 5.74 g of N-chlorosuccinimide in 250 ml of methylene chloride, maintaining the temperature of the mixture below 5° C. The mixture was then stirred for 5 minutes, after which 9 ml of triethylene were added dropwise, maintaining the temperature below 3° C. The reaction mixture was then treated in the same manner as described in Example 7, to give 4.5 g of the desired Compound 15HCl in the form of crystals melting at 230°–233° C. (with decomposition).

Elemental analysis: Calculated for $C_{12}H_{16}ClNS·HCl$: C, 51.80%; H, 6.15%; N, 5.03%; S, 11.52%, Cl, 25.48%. Found: C, 51.81%; H, 6.31%; N, 5.05%; S, 11.64%; Cl, 25.61%.

EXAMPLE 16

7,8-Dichloro-1,3,4,6-tetrahydro-6-methyl-2H-5,1-benzothiazocine hydrochloride (Compound 22HCl) and 8,9-dichloro-1,3,4,6-tetrahydro-6-methyl-2H-5,1-benzothiazocine (Compound 45)

5.3 g of 3,4-dichloro-N-(3-ethylthio)propylaniline were added to a solution of 2.7 g of N-chlorosuccinimide in 150 ml of methylene chloride, whilst maintaining the temperature below 7° C. The reaction mixture was then stirred for 5 minutes, after which 4 ml of triethylamine were added dropwise, again maintaining the temperature below 7° C. The reaction mixture was then treated as described in Example 1. Crystals obtained from the first fraction were recrystallized from a 3:2 by volume mixture of diethyl ether and petroleum ether to give 0.3 g of the 8,9-dichloro compound (Compound 45), melting at 89°–91° C.

Elemental analysis: Calculated for $C_{11}H_{13}Cl_2NS$: C, 50.39%; H, 5.00%; N, 5.34%; S, 12.23%; Cl, 27.04%. Found: C, 50.21%, H, 4.94%; N, 5.16%; S, 12.50%; Cl, 27.08%.

Oils from the second fraction were converted to the hydrochloride by conventional means and the resulting salt was recrystallized from a 1:1 by volume mixture of methanol and benzene to give 0.25 g of the 7,8-dichloro compound (Compound 22HCl), melting at 220°–222° C.

Elemental analysis: Calculated for $C_{11}H_{13}Cl_2NS·HCl$: C, 44.23%; H, 4.72%; N, 4.68%; S, 10.73%; Cl, 35.61%. Found: C, 44.03%; H, 4.32%; N, 4.58%; S, 10.96%; Cl, 35.84%.

EXAMPLE 17

8-Bromo-1,3,4,6-tetrahydro-6-methyl-2H-5,1-benzothiazocine hydrochloride (Compound 18HCl)

8.7 g of p-bromo-N-(3-ethylthio)propylaniline were added to a solution of 4.2 g of N-chlorosuccinimide in 200 ml of methylene chloride, maintaining the temperature below 4° C. After stirring the reaction mixture for 5 minutes, 6 ml of triethylamino were added dropwise, again maintaining the temperature below 4° C. The reaction mixture was then treated as described in Example 7, to give 6.2 g of the desired Compound 18HCl in the form of crystals melting at 220° C. (with decomposition).

Elemental analysis: Calculated for $C_{11}H_{14}BrNS·HCl$: C, 42.80%; H, 4.89%; N, 4.53%; S, 10.38%; Br, 25.88%; Cl, 11.48%; Found: C, 42.45%; H, 4.77%; N, 4.47%; S, 10.57%; Br, 25.77%; Cl, 11.44

EXAMPLE 18

1,3,4,6-Tetrahydro-8-iodo-6-methyl-2H-5,1-benzothiazocine hydrochloride (Compound 20HCl)

Following the same procedure as described in Example 17, but using N-(3-ethylthio)propyl-p-iodoaniline as the starting material, there was obtained the desired Compound 20HCl in the form of crystals.

EXAMPLE 19

1,3,4,6-Tetrahydro-6-methyl-8-nitro-2H-5,1-benzothiazocine (Compound 30)

4.8 g of N-(3-ethylthio)propyl-p-nitroaniline were added dropwise to a solution of 2.7 g of N-chlorosuccinimide in 150 ml of methylene chloride, whilst maintaining the temperaure below 10° C. The mixture was then stirred at 30° C. for 20 minutes, after which 4 ml of triethylamine were added dropwise, whilst maintaining the temperature below 7° C. After stirring the reaction mixture for 10 minutes, it was treated as described in Example 3 and the crude crystals thus obtained were recrystallized from a 3:2 by volume mixture of methylene chloride and n-hexane to give 1.2 g of the desired Compound 30 in the form of crystals melting at 138°–140° C.

Elemental analysis: Calculated for $C_{11}H_{14}N_2O_2S$: C, 55.44%; H, 5.92%; N, 11.75%; S, 13.45%. Found: C, 55.23%; H, 5.87%; N, 11.87%; S, 13.65%.

EXAMPLE 20

1,3,4,6-Tetrahydro-8-methanesulphonyl-6-methyl-2H-5,1-benzothiazocine (Compound 9)

Following the procedure of Example 19, but employing as starting material N-(3-ethylthio)propyl-p-methanesulphonylaniline, the desired Compound 9 was obtained in the form of crystals.

EXAMPLE 21

8-Cyano-1,3,4,6-tetrahydro-6-methyl-2H-5,1-benzothiazocine (Compound 40)

2.2 g of p-cyano-N-(3-ethylthio)propylaniline were added to a solution of 1.33 g of N chlorosuccinimide in 100 ml of methylene chloride, whilst maintaining the temperature below 8° C. 2 ml of triethylamine were then added dropwise to the solution, whilst maintaining the temperature below 6° C., after which the mixture was stirred for 5 minutes. The reaction mixture was then treated as described in Example 3 and the crude crystals thus obtained were recrystallized from a 3:2 by volume mixture of methylene chloride and n-hexane, to give 1.1 g of the desired Compound 40 in the form of crystals melting at 117°–119° C.

Elemental analysis: Calculated for $C_{12}H_{14}N_2S$: C, 66.01%; H, 6.46%; N, 12.83%; S, 14.68%. Found: C, 65.83%; H, 6.44%; N, 13.10%; S, 14.80%.

EXAMPLE 22

1,3,4,6-Tetrahydro-6-methyl-8-trifluoromethyl-2H-5,1-benzothiazocine (Compound 25)

4.3 g of N-(3-ethylthio)propyl-p-trifluoromethylaniline were added dropwise to a solution of 2.4 g of N-chlorosuccinimide in 150 ml of methylene chloride, maintaining the temperature below 10° C. The mixture was then stirred for 5 minutes, after which 3.5 ml of triethylamine were added dropwise, maintaining the mixture below 5° C. After stirring the reaction mixture for 5 minutes, it was treated as described in Example 3 to give 2.8 g of the desired Compound 25 in the form of crystals melting at 62°–64° C.

Elemental analysis: Calculated for $C_{12}H_{14}F_3NS$: C, 55.15%; H, 5.40%; N, 5.36%; S, 12.27%; F, 21.81%. Found: C, 55.23%; H, 5.56%; N, 5.21%; S, 12.54%; F, 21.59%.

EXAMPLE 23

6-Ethyl-1,3,4,6-tetrahydro-2H-5,1-benzothiazocine (Compound 46)

6.3 g of N-(3-propylthio)propylaniline were added dropwise to a solution of 4.0 g of N-chlorosuccinimide in 150 ml of methylene chloride, whilst maintaining the mixture below 10° C. The mixture was then stirred for 5 minutes, after which 8 ml of a 28% w/v methanolic solution of sodium methoxide was added dropwise, maintaining the temperature of the mixture below 8° C. After stirring the reaction mixture for 5 minutes, it was treated as described in Example 3, to give 3.4 g of the desired Compound 46 in the form of crystals melting at 38°–40° C.

Elemental analysis: Calculated for $C_{12}H_{17}NS$: C, 69.51%; H, 8.26%; N, 6.75%; S, 15.46%. Found: C, 69.61%; H, 8.27%; N, 6.77%; S, 15.54%.

EXAMPLE 24

1,2,3,4,5,7-Hexahydro-6,1-benzothiazonine (Compound 41)

1.95 g of N-(4-methylthio)butylaniline were added dropwise to a solution of 1.33 g of N-chlorosuccinimide in 50 ml of methylene chloride, whilst maintaining the temperature of the mixture below 5° C. The mixture was then stirred for 5 minutes, after which 2 ml of a 28% w/v methanolic solution of sodium methoxide was added dropwise, again maintaining the temperature below 5° C. After stirring the reaction mixture for 5 minutes, it was treated as described in Example 3 and the crude crystals so obtained were recrystallized from a 3:2 by volume mixture of methylene chloride and n-hexane, to give 1.7 g of the desired Compound 41 in the form of crystals melting at 91°–93° C.

Elemental analysis: Calculated for $C_{11}H_{15}NS$: C, 68.35%; H, 7.82%; N, 7.25%; S, 16.59%. Found: C, 68.22%; H, 7.85%; N, 7.01%; S, 16.51%.

EXAMPLE 25

1,2,3,4,5,7-Hexahydro-7-methyl-6,1-benzothiazonine (Compound 47)

10.5 g of N-(4-ethylthio)butylaniline were added dropwise to a solution of 6.7 g of N-chlorosuccinimide in 200 ml of methylene chloride, whilst maintaining the temperature of the mixture below 10° C. The mixture was then stirred for 5 minutes, after which 9 ml of triethylamine were added dropwise, whilst maintaining the temperature below 8° C. After stirring the reaction mixture for 10 minutes, it was treated as described in Example 3 and the crude oils obtained were distilled under reduced pressure to give 1.1 g of the desired Compound 47 in the form of an oil boiling at 108° C. (3 mmHg).

Elemental analysis: Calculated for $C_{12}H_{17}NS$: C, 69.51%; H, 8.26%; N, 6.75%; S, 15.46%. Found: C, 69.28%; H, 8.44%; N, 6.99%; S, 15.57%.

EXAMPLE 26

8-Chloro-1,3,4,6-tetrahydro-1,6-dimethyl-2H-5,1-benzothiazocine hydrochloride (Compound 17HCl)

A mixture of 500 mg of 8-chloro-1,3,4,6-tetrahydro-6-methyl-2H-5,1-benzothiazocine, 5 ml of formalin and 8 ml of formic acid was heated under reflux for 2 hours. The reaction mixture was then poured into water, made alkaline with sodium carbonate and extracted with chloroform. The extract was dried and then the solvent was evaporated off. The residue was purified by silica gel column chromatography and the oils so obtained were converted to the hydrochloride by conventional means. The resulting salt was recrystallized from a 1:1 by volume mixture of methanol and isopropanol to give 420 mg of the desired Compound 17HCl in the form of colourless prisms melting at 203° C. (with decomposition).

Elemental analysis: Calculated for $C_{12}H_{17}Cl_2NS$: C, 51.80%; H, 6.16%; N, 5.03%; S, 11.52%; Cl, 25.48%. Found: C, 52.12%; H, 6.20%; N, 4.93%; S, 11.37%; Cl, 25.71%.

EXAMPLE 27

8-Chloro-1,3,4,6-tetrahydro-1-methyl-2H-5,1-benzothiazocine (Compound 65)

Starting from 8-chloro-1,3,4,6-tetrahydro-2H-5,1-benzothiazocine (Compound 11), the same methylation as described in Example 26 was carried out to give the desired Compound 65 in the form of a pale yellow oil.

EXAMPLE 28

8-Chloro-1-ethyl-1,3,4,6-tetrahydro-6-methyl-2H-5,1-benzothiazocine hydrochloride (Compound 48HCl)

(a) 4 g of acetyl chloride were added dropwise to a suspension of 11.4 g of 8-chloro-1,3,4,6-tetrahydro-6-methyl-2H-5,1-benzothiazocine and 10 g of potassium carbonate in 100 ml of acetone, whilst keeping the temperature of the mixture below 10° C. The mixture was stirred for 30 minutes, after which it was poured into ice-water and extracted with chloroform. The solvent was evaporated from the extract and the residue was recrystallized from a 3:2 by volume mixture of methylene chloride and n-hexane to give 5 g of 1-acetyl-8-chloro-1,3,4,6-tetrahydro-6-methyl-2H-5,1-benzothiazocine in the form of crystals melting at 132°-135° C.

(b) 2.4 g of the 1-acetyl-8-chloro-1,3,4,6-tetrahydro-6-methyl-2H-5,1-benzothiazocine obtained in step (a) were added to a suspension of 1.5 g of lithium aluminium hydride in 100 ml of tetrahydrofuran, maintaining the temperature at 40°-50° C. The mixture was then stirred at the same temperature for 30 minutes, after which ethyl acetate and water were added. The mixture was filtered with the aid of a Celite (trade mark) filter aid and the solvent was evaporated from the resulting filtrate. The residue thus obtained was purified by silica gel column chromatography and the resulting oils were converted to the crystalline hydrochloride. This salt was recrystallized from methanol to give 1.7 g of the desired Compound 48 HCl in the form of crystals melting at 192°-195° C.

Elemental analysis:

Calculated for $C_{13}H_{19}Cl_2NS$: C, 53.42%; H, 6.55%; N, 4.79%; S, 10.97%; Cl, 24.26%. Found: C, 53.39%; H, 6.59%; N, 4.81%; S, 11.03%; Cl, 24.29%.

EXAMPLE 29

1,3,4,6-Tetrahydro-2H-5,1-benzothiazocine 3.6 g of N-(3-methylthio)propylaniline were added to a solution of 2.7 g of N-chlorosuccinimide in 200 ml of chloroform, whilst maintaining the mixture at a temperature below 10° C. After stirring the reaction mixture for 5 minutes, the solvent was distilled off under reduced pressure to give 6.0 g of crystals comprising a equimolar mixture of 1-methyl-2-phenylisothiazolidium chloride and succinimide. These crystals decomposed at 80° C. and were hygroscopic.

Nuclear magnetic resonance spectrum (deuterated chloroform) δ ppm:
2.9 (multiplet, 2H, $CH_2$);
3.30 (singlet, 3H, —S—$CH_3$);
4.05 (multiplet, 2H, N—$CH_2$—);
4.50 (triplet, J=7 Hz, 2H, —S—$CH_2$—);
7.0-7.5 (multiplet, 5H, $C_6H_5$).

This crystalline mixture was dissolved in 100 ml of chloroform and then 4 ml of a 28% w/v methanolic solution of sodium methoxide were added. The reaction mixture was stirred for 5 minutes, after which it was washed with water and dried over sodium sulphate. The solvent was then distilled off and the residue was purified by silica gel column chromatography (eluted with benzene). The product was recrystallized from a 3:2 by volume mixture of diethyl ether and n-hexane, to give 3.2 g of the desired compound as crystals melting at 77°-79° C.

Elemental analysis: Calculated for $C_{10}H_{13}NS$: C, 66.99%; H, 7.31%; N, 7.81%; S, 17.88%. Found: C, 66.89%; H, 7.26%; N, 7.54%; S, 18.00%.

EXAMPLES 30-32

Following the same procedure as described in Example 29, and, where appropriate, converting the product to the hydrochloride before isolation, the following compounds were obtained:

1,3,4,6-tetrahydro-8-methoxy-2H-5,1-benzothiazocine hydrochloride (Compound 8HCl), melting point 215°-218° C. (with decomposition);

1,3,4,6-tetrahydro-8-nitro-2H-5,1-benzothiazocine (Compound 49), melting point 160°-162° C.;

8-cyano-1,3,4,6-tetrahydro-2H-5,1-benzothiazocine (Compound 50), melting point 136°-139° C.

EXAMPLE 33

1,3,4,6-Tetrahydro-2H-5,1-benzothiazocine-S-oxide (Compound 51)

1.2 g of 1,3,4,6-tetrahydro-2H-5,1-benzothiazocine were dissolved in 100 ml of methanol, and then a solution of 1.2 g of sodium metaperiodate in 50 ml of water was added dropwise at room temperature. After stirring the reaction mixture for 1 hour, it was poured into ice-water and extracted with methylene chloride. The solvent was evaporated from the extract and the residue was recrystallized from methanol to give 1.1 g of the desired Compound 51 in the form of crystals melting at 123°–124° C.

Elemental analysis: Calculated for $C_{10}H_{13}NOS$: C, 61.50%; H, 6.71%; N, 7.17%; S, 16.41%. Found: C, 61.34%; H, 6.67%; N, 7.05%; S, 16.42%.

EXAMPLE 34

1,3,4,6-Tetrahydro-8-methyl-2H-5,1-benzothiazocine-S-oxide (Compound 52)

A solution of 3.5 g of sodium metaperiodate in 100 ml of water was added dropwise at room temperature to a solution of 2.7 g of 1,3,4,6-tetrahydro-8-methyl-2H-5,1-benzothiazocine in 100 ml of methanol. After stirring the reaction mixture for 30 minutes, it was treated as described in Example 33, and the crude product was recrystallized from a 3:2 by volume mixture of methylene chloride and n-hexane to give 2.7 g of the desired Compound 52 in the form of crystals melting at 131°–134° C. (with decomposition).

Elemental analysis: Calculated for $C_{11}H_{15}NOS$: C, 63.12%; H, 7.22%; N, 6.69%; S, 15.31%. Found: C, 62.82%; H, 7.16%; N, 6.60%; S, 15.41%.

EXAMPLE 35

1,3,4,6-Tetrahydro-8-methoxy-2H-5,1-benzothiazocine-S-oxide (Compound 62)

A solution of 2.5 g of sodium metaperiodate in 100 ml of water was added dropwise at room temperature to a solution of 2.2 g of 1,3,4,6-tetrahydro-8-methoxy-2H-5,1-benzothiazocine in 100 ml of methanol and the mixture was stirred for 1 hour. The mixture was then treated as described in Example 33 and the resulting crude product was recrystallized from a 3:2 by volume mixture of methylene chloride and benzene, to give 1.8 g of the desired Compound 62 in the form of crystals melting at 155°–157° C.

Elemental analysis: Calculated for $C_{11}H_{15}NO_2S$: C, 58.63%; H, 6.71%; N, 6.21%; S, 14.23%. Found: C, 58.29%; H, 6.54%; N, 6.14%; S, 14.16%.

EXAMPLE 36

8-Fluoro-1,3,4,6-tetrahydro-2H-5,1-benzothiazocine-S-oxide (Compound 53)

A solution of 4 g of sodium metaperiodate in 100 ml of water was added dropwise at room temperature to a solution of 3.7 g of 8-fluoro-1,3,4,6-tetrahydro-2H-5,1-benzothiazocine in 100 ml of methanol and the mixture was stirred for 30 minutes. It was then treated as described in Example 33 and the resulting crude product was recrystallized from a 3:2 by volume mixture of methylene chloride and benzene to give 3.4 g of the desired Compound 53 in the form of crystals melting at 117°–119° C.

Elemental analysis: Calculated for $C_{10}H_{12}NOS$: C, 56.31%; H, 5.67%; N, 6.56%; F, 8.90%; S, 15.03%. Found: C, 56.11%; H, 5.54%; N, 6.52%; F, 8.65%; S, 14.70%.

EXAMPLE 37

8-Chloro-1,3,4,6-tetrahydro-2H-5,1-benzothiazocine-S-oxide (Compound 54)

A solution of 10 g of sodium metaperiodate in 200 ml of water was added dropwise at room temperature to a solution of 8.4 g of 8-chloro-1,3,4,6-tetrahydro-2H-5,1-benzothiazocine in 200 ml of methanol and the mixture was stirred for 30 minutes. The mixture was then treated as described in Example 33 and the resulting crude product was recrystallized from a 1:1 by volume mixture of methylene chloride and acetone to give 7.4 g of the desired Compound 54 in the form of crystals melting at 196°–198° C. (with decomposition).

Elemental analysis: Calculated for $C_{10}H_{12}ClNOS$: C, 52.28%; H, 5.26%; N, 6.09%; Cl, 15.43%; S, 13.95%. Found: C, 52.18%; H, 5.49%; N, 6.07%; Cl, 15.84%; S, 14.15%.

EXAMPLE 38

1,3,4,6-Tetrahydro-8-nitro-2H-5,1-benzothiazocine-S-oxide (Compound 60)

A solution of 2 g of sodium metaperiodate in 200 ml of water was added dropwise to a solution of 2.2 g of 1,3,4,6-tetrahydro-8-nitro-2H-5,1-benzothiazocine in 200 ml of methanol. After stirring the mixture at room temperature for 1 hour, it was then treated as described in Example 33 and the crude product was recrystallized from methanol to give 1.8 g of the desired Compound 60 in the form of crystals melting at 233°–235° C. (with decomposition).

Elemental analysis: Calculated for $C_{10}H_{12}N_2O_3S$: C, 49.98%; H, 5.03%; N, 11.65%; S, 13.34%. Found: C, 49.75%; H, 5.00%; N, 11.66%; S, 13.55%.

EXAMPLE 39

8-Cyano-1,3,4,6-tetrahydro-2H-5,1-benzothiazocine-S-oxide (Compound 61)

A solution of 0.5 g of sodium metaperiodate in 50 ml of water was added dropwise to a solution of 0.4 g of 8-cyano-1,3,4,6-tetrahydro-2H-5,1-benzothiazocine in 50 ml of methanol. After stirring the reaction mixture at room temperature for 1 hour, it was treated as described in Example 33 and the crude product was recrystallized from methanol to give 0.35 g of the desired Compound 61 in the form of crystals melting at 234°–236° C. (with decomposition).

Elemental analysis: Calculated for $C_{11}H_{12}N_2OS$: C, 59.97%; H, 5.49%; N, 12.71%; S, 14.55%; Found: C, 59.92%; H, 5.33%; N, 12.48%; S, 14.63%.

EXAMPLE 40

8-Bromo-1,3,4,6-tetrahydro-6-methyl-2H-5,1-benzothiazocine-S-oxide (Compound 55)

1.9 g of m-chloroperbenzoic acid were added to a solution of 2.2 g of 8-bromo-1,3,4,6-tetrahydro-6-methyl-2H-5,1-benzothiazocine in 100 ml of chloroform. After stirring the reaction mixture for 2 hours, it was washed with, in turn, aqueous sodium hydrogen carbonate and water and then dried. The solvent was evaporated off under reduced pressure to give 2.1 g of the desired Compound 55 in the form of an oil. Mass spectrum m/e 287 (M+) ($C_{11}H_{14}BrNOS$).

Nuclear magnetic resonance spectrum (deuterated chloroform ) δ ppm:
1.75 (doublet, 3H, CH$_3$);
1.5–4.0 [multiplet, 6H, —(CH$_2$)$_3$—];
4.80 (quartet, 0.4H, —CHCH$_3$);
4.88 (quartet, 0.6H, —CHCH$_3$);
6.9–7.6 (multiplet, 3H, benzene ring).

EXAMPLE 41

1,2,3,4,5,7-Hexahydro-6,1-benzothiazonine-S-oxide (Compound 64)

A solution of 2.0 g of sodium metaperiodate in 50 ml of water was added dropwise at room temperature to a solution of 1.5 g of 1,2,3,4,5,7-hexahydro-6,1-benzothiazenine in 100 ml of methanol. After the reaction was complete, the reaction mixture was treated as described in Example 33 and the resulting crude product was recrystallized from a 3:2 by volume mixture of methylene chloride and benzene to give 1.2 g of the desired Compound 64 in the form of crystals melting at 130°–132° C. (with decomposition).

Elemental analysis: Calculated for $C_{11}H_{15}NOS$: C, 63.12%; H, 7.22%; N, 6.69%; S, 15.31%. Found: C, 63.02%; H, 7.11%; N, 6.64%; S, 15.34%.

EXAMPLE 42

8-Chloro-1,3,4,6-tetrahydro-1-methyl-2H-5,1-benzethiazocine-S-oxide (Compound 63)

2.3 g of 8-chloro-1,3,4,6-tetrahydro-1-methyl-2H-5,1-benzothiazocine were dissolved in 100 ml of methanol, and a solution of 2.6 g of sodium metaperiodate in 100 ml of water was added dropwise at room temperature. After stirring for 30 minutes, the reaction mixture was treated as described in Example 33 and the resulting crude product was recrystallized from diisopropyl ether to give 1.5 g of the desired Compound 63 in the form of crystals melting at 89°–91° C.

Elemental analysis: Calculated for $C_{11}H_{14}ClNOS$: C, 54.20%; H, 5.79%; N, 5.75%; Cl, 14.54%; S, 13.15%. Found: C, 54.26%; H, 5.78%; N, 5.63%; Cl, 14.53%; S, 13.31%.

PREPARATION 1 (Method A)

3-Ethylthiopropionic p-propylanilide 6 g of 3-ethylthiopropionyl chloride were added dropwise to a mixture of 6 g of p-propylaniline, 4 g of potassium carbonate and 200 ml of acetone. The mixture was refluxed for 30 minutes and then poured into ice-water. After acidifying the mixture with hydrochloric acid, it was extracted with diethyl ether. The diethyl ether was distilled off to give 7.6 g of the desired product in the form of an oil.

PREPARATION 2 (Method B)

3-Ethylthiopropionic anilide 25 ml of a 28% w/v aqueous solution to the sodium salt of ethylmercaptan were added to a solution of 9.2 g of 3-chloropropionic anilide in 150 ml of dioxan, and the mixture was refluxed for 1 hour. After completion of the reaction, the reaction mixture was poured into ice-water and the precipitates produced were collected by filtration and recrystallized from benzene to give 8 g of the desired compound in the form of crystals melting at 45°–46° C.

PREPARATIONS 3–17

Following either Method A or B, as described in the above Preparations, a series of ω-substituted thioaliphatic acid anilide derivatives was obtained. The products obtained, their properties and the reaction conditions are summarized in Table 2.

TABLE 2

ω-Substituted thioaliphatic acid anilide derivatives

| Preparation | $X^1$ | $X^2$ | $R^1$ | $R^2$ | n | Melting Point °C. (Boiling Point °C.) |
|---|---|---|---|---|---|---|
| 3 | 4-CH₃ | H | H | H | 1 | oil |
| 4 | 4-OCH₃ | H | H | H | 1 | 89–91 |
| 5 | 4-F | H | H | H | 1 | oil |
| 6 | 3-Cl | H | H | H | 1 | oil |
| 7 | 4-Cl | H | H | H | 1 | 87–89 |
| 8 | 4-n-C₄H₉ | H | H | CH₃ | 1 | oil |
| 9 | 3-CH₃ | 4-CH₃ | H | CH₃ | 1 | oil |
| 10 | 4-F | H | H | CH₃ | 1 | oil |
| 11 | 2-Cl | H | H | CH₃ | 1 | 80–82 |

| Preparation | Method | Reaction conditions |
|---|---|---|
| 3 | A | reflux, 1 hour |
| 4 | B | reflux, 1 hour |
| 5 | A | reflux, 1 hour |
| 6 | A | reflux, 0.5 hour |
| 7 | B | reflux, 1 hour |
| 8 | A | reflux, 0.5 hour |
| 9 | A | reflux, 0.5 hour |
| 10 | A | relux, 0.5 hour |
| 11 | B | room temperature, 5 hours |

| Preparation | $X^1$ | $X^2$ | $R^1$ | $R^2$ | n | Melting Point °C. (Boiling Point °C.) |
|---|---|---|---|---|---|---|
| 12 | 4-Cl | H | CH₃ | CH₃ | 1 | 100–102 |
| 13 | 4-Br | H | H | CH₃ | 1 | 83–85 |
| 14 | 3-Cl | 4-Cl | H | CH₃ | 1 | oil |
| 15 | 4-CF₃ | H | H | CH₃ | 1 | 73–75 |
| 16 | H | H | H | H | 2 | (200/1 mmHg) |
| 17 | H | H | H | CH₃ | 2 | oil |

| Preparation | Method | Reaction conditions |
|---|---|---|
| 12 | A | reflux, 0.5 hour |
| 13 | A | reflux, 0.5 hour |
| 14 | A | reflux, 0.5 hour |
| 15 | B | room temperature, 3 hours |
| 16 | B | room temperature, 2 days |
| 17 | B | room temperature, 3 days |

PREPARATION 18 (Method C)

p-Chloro-N-(3-methylthio)propylaniline 16 g of lithium aluminium hydride were added to a mixture of 90 g of 3-methylthiopropionic p-chloroanilide and 700 ml of tetrahydrofuran. The mixture was then refluxed for 5 hours, after which water was added to the reaction mixture and insolubles were filtered off using a Celite filter aid. The solvent was then evaporated off from the filtrate and the oily residue was distilled under reduced pressure to give 43 g of the desired compound in the form of oils boiling at 165° C. (2 mmHg).

PREPARATION 19 (Method D)

p-Cyano-N-(3-methylthio)propylaniline

A mixture of 12 g of p-cyanoaniline, 12 g of 3-methylthiopropyl chloride and a small amount of potassium iodide in 200 ml of dimethylformamide was refluxed for 3 hours. At the end of this time, the reaction mixture was poured into ice-water and extracted with diethyl ether. The extract was washed with water and dried and then the solvent was evaporated off under reduced pressure. The residue was purified by silica gel column chromatography, after which it was distilled under reduced pressure to give 1.2 g of the desired product in the form of an oil boiling at 220°–230° C. (4 mmHg).

PREPARATION 20 (Method E)

p-Chloro-N-(3-ethylthio)propylaniline

A mixture of 50 g of p-chloroacetanilide, 7.5 g of sodium hydride and 300 ml of dimethylformamide was stirred at room temperature for 30 minutes. At the end of this time, 45 g of 3-ethylthiopropyl chloride were added and the mixture was heated at 100°–120° C. for 2 hours. The reaction mixture was then poured into ice-water and extracted with diethyl ether. The solvent was then evaporated from the extract under reduced pressure and the residue was refluxed with 500 ml of concentrated hydrochloric acid for 7 hours. The reaction mixture was then washed with diethyl ether, made alkaline by the addition of a 10% w/v aqueous solution of sodium hydroxide and extracted with diethyl ether. The solvent was evaporated from the extract under reduced pressure to give 40 g of the desired compound in the form of an oil boiling at 165°–170° C. (3 mmHg).

PREPARATIONS 21–43

Following the procedures of Methods C, D or E, as described in the above Preparations, a series of ω-substituted thioalkylaniline derivatives was prepared, as summarised in Table 3.

TABLE 3

ω-Substituted thioalkylaniline derivatives

| Preparation | $X^1$ | $X^2$ | $R^1$ | $R^2$ | n | Boiling Point °C./mmHg | Method |
|---|---|---|---|---|---|---|---|
| 21 | 4-$CH_3$ | H | H | H | 1 | 172–174/10 | C |
| 22 | 4-$OCH_3$ | H | H | H | 1 | 150–160/0.3 | C |
| 23 | 4-F | H | H | H | 1 | oil | C |
| 24 | 3-Cl | H | H | H | 1 | 173/5 | C |
| 25 | 4-$NO_2$ | H | H | H | 1 | oil | E |
| 26 | H | H | H | $CH_3$ | 1 | 143/3 | C |
| 27 | 4-$CH_3$ | H | H | $CH_3$ | 1 | 150–160/3 | D |
| 28 | 4-$C_2H_5$ | H | H | $CH_3$ | 1 | 165–170/5 | D |
| 29 | 4-$C_3H_7$ | H | H | $CH_3$ | 1 | 180/7 | C |
| 30 | 4-$C_4H_9$ | H | H | $CH_3$ | 1 | 185–187/3 | C |
| 31 | 3-$CH_3$ | 4-$CH_3$ | H | $CH_3$ | 1 | 170–175/3 | C |
| 32 | 4-F | H | H | $CH_3$ | 1 | 152/4 | C |
| 33 | 2-Cl | H | H | $CH_3$ | 1 | 155–158/3 | C |
| 34 | 3-Cl | H | H | $CH_3$ | 1 | 143–145/3 | D |
| 35 | 4-Cl | H | $CH_3$ | $CH_3$ | 1 | 180/5 | C |
| 36 | 3-Cl | 4-Cl | H | $CH_3$ | 1 | 195–200/3 | C |
| 37 | 4-Br | H | H | $CH_3$ | 1 | 180/5 | C |
| 38 | 4-$CF_3$ | H | H | $CH_3$ | 1 | 150–160/3 | C |
| 39 | 4-$NO_2$ | H | H | $CH_3$ | 1 | oil | E |
| 40 | 4-CN | H | H | $CH_3$ | 1 | 220/3 | D |
| 41 | H | H | H | $CH_3CH_2$ | 1 | 140–150/0.5 | D |
| 42 | H | H | H | H | 2 | 140/1 | C |
| 43 | H | H | H | $CH_3$ | 2 | 155–158/3 | C |

We claim:
1. Compounds of formula (I):

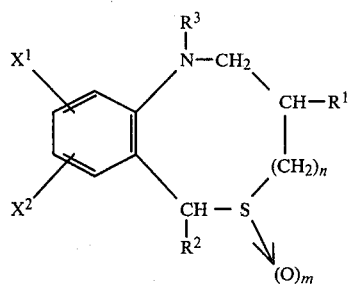

wherein:
$R^1$ and $R^2$ are the same or different and each represents a hydrogen atom or a methyl group;
$R^3$ is a hydrogen atom or an alkyl group having from 1 to 4 carbon atoms;
$X^1$ is a hydrogen atom, a methyl group, a methoxy group, a methanesulfonyl group, a halogen atom, a trifluoromethyl group, a nitro group or a cyano group at the 7-, 8-, or 9-position;
$X^2$ is a hydrogen atom;
n is 1 or 2; and
m is 0 or 1;
and pharmaceutically acceptable acid addition salts thereof;
excluding those compounds in which:
$R^1$, $R^2$, $R^3$, $X^1$ and $X^2$ all represent hydrogen atoms, n is 1 and m is 0; and
$R^1$, $R^2$ and $X^2$ all represent hydrogen atoms, $R^3$ represents a hydrogen atom or a methyl group, $X^1$ represents a chlorine atom at the 9-position, n is 1 and m is 0.

2. Compounds as claimed in claim 1, wherein:
$R^1$, $R^2$ and $R^3$ are the same or different and each represents a hydrogen atom or a methyl group;
$X^1$ is a methyl group, a methanesulfonyl group, a halogen atom, trifluoromethyl group, a nitro group or a cyano group at the 7-, 8- or 9-position;
$X^2$ represents a hydrogen atom;
n is 1; and
m is 0 or 1.

3. Compounds as claimed in claim 1, wherein:
$R^1$ and $R^3$ are the same or different and each represents a hydrogen atom or a methyl group;
$R^2$ represents a methyl group;
$X^1$ represents a substituent at the 8-position, said substituent being selected from a methanesulfonyl group, a halogen atom, a trifluoromethyl group, a nitro group or a cyano group;
$X^2$ represents a hydrogen atom;
n is 1; and
m is 0 or 1.

4. Compounds as claimed in claim 1, wherein:
$R^1$, $R^2$ and $R^3$ all represent hydrogen atoms;
$X^1$ represents a hydrogen atom, a methoxy group, or a halogen atom at the 7- or 8-position;
$X^2$ represents a hydrogen atom;
n is 1; and
m is 1.

5. 1,3,4,6-Tetrahydro-8-methanesulphonyl-6-methyl-2$\underline{H}$-5,1-benzothiazocine and its hydrochloride of the formula of claim 1.

6. 8-Fluoro-1,3,4,6-tetrahydro-6-methyl-2$\underline{H}$-5,1-benzothiazocine and its hydrochloride of the formula of claim 1.

7. 8-Chloro-1,3,4,6-tetrahydro-6-methyl-2H-5,1-benzothiazocine and its hydrochloride of the formula of claim 1.

8. 8-Chloro-1,3,4,6-tetrahydro-3,6-dimethyl-2H-5,1-benzothiazocine and its hydrochloride of the formula of claim 1.

9. 8-Chloro-1,3,4,6-tetrahydro-1,6-dimethyl-2H-5,1-benzothiazocine and its hydrochloride of the formula of claim 1.

10. 8-Bromo-1,3,4,6-tetrahydro-6-methyl-2H-5,1-benzothiazocine and its hydrochloride of the formula of claim 1.

11. 1,3,4,6-Tetrahydro-8-iodo-6-methyl-2H-5,1-benzothiazocine and its hydrochloride of the formula of claim 1.

12. 1,3,4,6-Tetrahydro-6-methyl-8-trifluoromethyl-2H-5,1-benzothiazocine and its hydrochloride of the formula of claim 1.

13. 1,3,4,6-Tetrahydro-6-methyl-8-nitro-2H-5,1-benzothiazocine and its hydrochloride of the formula of claim 1.

14. 8-Cyano-1,3,4,6-tetrahydro-6-methyl-2H-5,1-benzothiazocine and its hydrochloride of the formula of claim 1.

15. 1,3,4,6-Tetrahydro-2H-5,1-benzothiazocine-S-oxide of the formula of claim 1.

16. 8-Fluoro-1,3,4,6-tetrahydro-2H-5,1-benzothiazocine-S-oxide of the formula of claim 1.

17. 8-Chloro-1,3,4,6-tetrahydro-2H-5,1-benzothiazocine-S-oxide of the formula of claim 1.

18. 8-Bromo-1,3,4,6-tetrahydro-6-methyl-2H-5,1-benzothiazocine-S-oxide of the formula of claim 1.

19. 1,3,4,6-Tetrahydro-8-trifluoromethyl-2H-5,1-benzothiazocine-S-oxide of the formula of claim 1.

20. 1,3,4,6-Tetrahydro-8-nitro-2H-5,1-benzothiazocine-S-oxide of the formula of claim 1.

21. 8-Cyano-1,3,4,6-tetrahydro-2H-5,1-benzothiazocine-S-oxide of the formula of claim 1.

22. 1,3,4,6-Tetrahydro-8-methoxy-2H-5,1-benzothiazocine-S-oxide of the formula of claim 1.

23. 9-Chloro-1,3,4,6-tetrahydro-6-methyl-2H-5,1-benzothiazocine of the formula of claim 1.

24. 7-Chloro-1,3,4,6-tetrahydro-6-methyl-2H-5,1-benzothiazocine of the formula of claim 1.

25. A pharmaceutical composition comprising a pharmaceutically acceptable carrier or a diluent and, as active ingredient, a compound of formula (I):

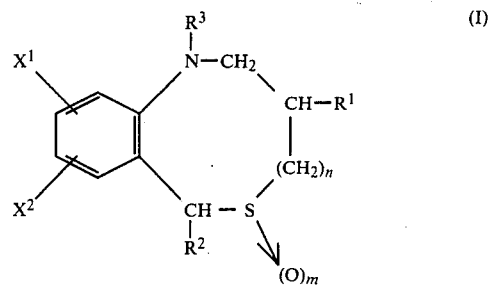

wherein:
$R^1$ and $R^2$ are the same or different and each represents a hydrogen atom or a methyl group;
$R^3$ is a hydrogen atom or an alkyl group having from 1 to 4 carbon atoms;
$X^1$ is a hydrogen atom, a methyl group, a methoxy group, a methanesulfonyl group, a halogen atom, a trifluoromethyl group, a nitro group or a cyano group at the 7-, 8- or 9-position;
$X^2$ is a hydrogen atom;
n is 1 or 2; and
m is 0 or 1;
or a pharmaceutically acceptable acid addition salt thereof;
excluding those compounds in which:
$R^1$, $R^2$, $R^3$, $X^1$ and $X^2$ all represent hydrogen atoms, n is 1 and m is 0; and
$R^1$, $R^2$ and $X^2$ all represent atoms, $R^3$ represents a hydrogen atom or a methyl group, $X^1$ represents a chlorine atom at the 9-position, n is 1 and m is 0.

26. A composition as claimed in claim 25, wherein:
$R^1$, $R^2$ and $R^3$ are the same or different and each represents a hydrogen atom or a methyl group;
$X^1$ is a methyl group, a methanesulfonyl group, a halogen atom, trifluoromethyl group, a nitro group or a cyano group at the 7-, 8- or 9-position;
$X^2$ represents a hydrogen atom;
n is 1; and
m is 0 or 1.

27. A composition as claimed in claim 25, wherein:
$R^1$ and $R^3$ are the same or different and each represents a hydrogen atom or a methyl group;
$R^2$ represents a methyl group;
$X^1$ represents a substituent at the 8-position, said substituent being selected from a methanesulfonyl group, a halogen atom, a trifluoromethyl group, a nitro group or a cyano group;
$X^2$ represents a hydrogen atom;
n is 1; and
m is 0 or 1.

28. A composition as claimed in claim 25, wherein $R^1$, $R^2$ and $R^3$ all represent hydrogen atoms;
$X^1$ represents a hydrogen atom, a methoxy group, or a halogen atom at the 7- or 8-position;
$X^2$ represents a hydrogen atom;
n is 1; and
m is 1.

* * * * *

UNITED STATES PATENT AND TRADEMARK OFFICE
CERTIFICATE OF CORRECTION

PATENT NO. : 4,328,238

DATED : May 4, 1982

INVENTOR(S) : YASUNOBU SATO et al

It is certified that error appears in the above—identified patent and that said Letters Patent is hereby corrected as shown below:

Column 9, line 1: delete "mixutre" and insert --mixture--.

Column 10, line 5: delete "880" and insert --860--.

Column 10, line 34: delete "vontacting" and insert --contacting--.

Column 26, lines 29-34: delete all of the subject matter on these lines and insert the following:

-- $R^1$, $R^2$, and $R^3$ all represent hydrogen atoms, $X^1$ represents a hydrogen atom or a methanesulfonyl group at the 8-position, n is 1 and m is 0; and $R^1$ and $R^2$ all represent hydrogen atoms, $R^3$ represents a hydrogen atom or a methyl group, $X^1$ represents a chlorine atom at the 9-position, n is 1 and m is 0.

UNITED STATES PATENT AND TRADEMARK OFFICE
CERTIFICATE OF CORRECTION

PATENT NO. : 4,328,238

DATED : May 4, 1982

INVENTOR(S) : YASUNOBU SATO et al

It is certified that error appears in the above—identified patent and that said Letters Patent is hereby corrected as shown below:

Column 28, lines 29-33: delete all of the subject matter on these lines and insert the following:

-- $R^1$, $R^2$, and $R^3$ all represent hydrogen atoms, $X^1$ represents a hydrogen atom or a methanesulfonyl group at the 8-position, n is 1 and m is 0; and $R^1$ and $R^2$ all represent hydrogen atoms, $R^3$ represents a hydrogen atom or a methyl group, $X^1$ represents a chlorine atom at the 9-position, n is 1 and m is 0.

Signed and Sealed this

Fifth Day of October 1982

[SEAL]

Attest:

GERALD J. MOSSINGHOFF

Attesting Officer   Commissioner of Patents and Trademarks